(12) United States Patent
Tai et al.

(10) Patent No.: US 7,252,006 B2
(45) Date of Patent: Aug. 7, 2007

(54) IMPLANTABLE MECHANICAL PRESSURE SENSOR AND METHOD OF MANUFACTURING THE SAME

(75) Inventors: Yu-Chong Tai, Pasadena, CA (US); Ellis Meng, Pasadena, CA (US); Po-Jui Chen, Pasadena, CA (US); Damien C. Rodger, Los Angeles, CA (US); Mark Humayun, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/148,124

(22) Filed: Jun. 7, 2005

(65) Prior Publication Data

US 2005/0268722 A1    Dec. 8, 2005

Related U.S. Application Data

(60) Provisional application No. 60/578,052, filed on Jun. 7, 2004.

(51) Int. Cl.
*G01L 9/00* (2006.01)

(52) U.S. Cl. .......................................... 73/700; 600/486
(58) Field of Classification Search .................. 73/732, 73/743, 700; 374/131; 600/486; 604/9
See application file for complete search history.

(56) References Cited

U.S. PATENT DOCUMENTS

| | | | | |
|---|---|---|---|---|
| 4,986,671 | A * | 1/1991 | Sun et al. ................... | 374/131 |
| 2005/0043670 | A1* | 2/2005 | Rosenberg ................. | 604/9 |
| 2005/0043679 | A1* | 2/2005 | Devens et al. ......... | 604/103.06 |
| 2005/0288604 | A1 | 12/2005 | Eigler et al. | |
| 2006/0106370 | A1* | 5/2006 | Baerveldt et al. .......... | 606/4 |

OTHER PUBLICATIONS

International Search Report for International Application No. PCT/US2005/020244, filed Jun. 7, 2005, completed Jul. 21, 2006, mailed Aug. 31, 2006, 2 pgs.
Written Opinion for International Application No. PCT/US2005/020244, filed Jun. 7, 2005, completed Jul. 21, 2006, mailed Aug. 31, 2006, 3 pgs.
Wolf, "An Elementary Theory of the Bourdon Gage", Journal of Applied Mechanics, Sep. 1946, pp. A207-A210.
Clark et al, "Deformations and Stresses in Bourdon Tubes", Journal of Applied Physics, Dec. 1950, vol. 21, pp. 1340-1341.
Dressler, "Elastic Shell-Theory Formulation for Bourdon Tubes", Transactions of the ASME, Journal of Basic Engineering, Dec. 1965, pp. 1072-1078.
Yao, "Parylene for MEMS Applications", Thesis Chapter 2 entitled Parylene as a MEMS Material, 2002, pp. 23-75.

* cited by examiner

*Primary Examiner*—Andre J. Allen
(74) *Attorney, Agent, or Firm*—Christie, Parker & Hale, LLP

(57) ABSTRACT

A biocompatible, mechanical, micromachined pressure sensor and methods of manufacturing such a pressure sensor are provided. The pressure sensor of the current invention includes a high-aspect-ratio curved-tube structure fabricated through a one-layer parylene process. The pressure sensor of the current invention requires zero power consumption and indicates the pressure variation by changes of the in situ in-plane motion of the sensor, which can be gauged externally by a direct and convenient optical observation. In one embodiment, the pressure sensor of the current invention has been shown to work as an IOP sensor for eye implantation where the intraocular in-plane motion of the sensor can be recorded from outside of the eye, such that the intraocular pressure in glaucoma patients can be constantly monitored.

26 Claims, 16 Drawing Sheets

IMPLANTABLE MECHANICAL PRESSURE SENSOR AND METHOD OF MANUFACTURING THE SAME

CROSS-REFERENCE TO RELATED APPLICATION(S)

This application claims priority to U.S. Provisional Patent Application No. 60/578,052, filed Jun. 7, 2004, the disclosure of which is incorporated herein by reference.

STATEMENT REGARDING FEDERALLY SPONSORED RESEARCH

The U.S. Government has certain rights in this invention pursuant to grant number EEC-0310723, awarded by the National Science Foundation, Engineering Research Centers Program.

FIELD OF THE INVENTION

The current invention is directed to an implantable optical pressure sensors; and more particularly to an implantable mechanical intraocular pressure sensor for passive measurement of the intraocular pressure and methods of manufacturing such sensors.

BACKGROUND OF THE INVENTION

Glaucoma is a debilitating disease that results in loss of vision for an estimated 65 million people worldwide. Glaucoma is the second leading cause of blindness in the U.S. and the leading cause of preventable blindness. Yet, only half of the people with Glaucoma know they have the disease. Glaucoma is principally defined by damage to the optic nerve, the ultimate pathway for visual information after processing by the retina at the posterior aspect of the eye. Of the many risk factors for this optic neuropathy, perhaps the most significant is elevated intraocular pressure (IOP). Because IOP is strongly implicated in the pathogenesis of glaucoma, and because treatment involves lowering patients' IOP, methods of precisely monitoring real-time pressure changes are critical for treatment of this disease. This task is complicated by the very sensitive pressure measurements required to detect abnormal pressures in the eye (e.g., normal eye pressure typically ranges from 10–21 mmHg, averaging about 15 mmHg with a ±mmHg deviation), and the invasive nature of current intraocular pressure sensors.

There is no known sensor on the market for the constant real-time measurement of these small intraocular pressures. The potential of such a sensor is that measurements can be made for years for ongoing monitoring of glaucoma treatment. For example, current tonometry techniques involve indirect measurement of IOP. The tonometers used in common practice are difficult to implement for regularly monitoring pressure fluctuations and treatment progress because they rely on skilled operators using external measurement devices that requires constant out-patient treatment and provides only intermittent monitoring of the IOP. In response to the deficiency of current measurement methods, many micromachined or "MEMS" pressure sensor designs have been proposed. MEMS devices are of interest because in principal the small scale of MEMS devices allows for the implantation of a sensor for constant IOP monitoring. These microfabricated devices can provide accurate and precise pressure readouts, but conventional designs all require electrical circuitry and hermetic sealing, a significant impediment to their implementation. None of the IOP sensors proposed solve the two principal difficulties of these devices; power consumption and biocompatibility.

Accordingly, an improved sensor for providing faithful IOP measurement inside the eye without the twin problems of power consumption and biocompatibility is needed.

SUMMARY OF THE INVENTION

The current invention is directed to a passive, biocompatible micromachined pressure sensor comprising a micromachined curved tube that contracts and expands in response to changes in pressure.

In one embodiment, the sensor comprises an implantable micromachined Bourdon tube. In such an embodiment the sensor can be implanted under the cornea so that IOP changes can be constantly monitored.

In another exemplary embodiment, the sensor in accordance with the current invention can be measured passively through optical inspection of the device using standard ophthalmologic equipment, such as stereoscopes and magnifiers.

In yet another exemplary embodiment, the sensor in accordance with the current invention has a 1 mmHg resolution and a ±6 mmHg dynamic range.

In still another exemplary embodiment, the invention is directed to a method of manufacturing a sensor in accordance with the current invention. In one such embodiment, the sensor is made using standard micromachining techniques in a simple two mask process.

In still yet another exemplary embodiment, the sensor in accordance with the current invention is formed of a USP Class VI biocompatible material. In one such embodiment the biocompatible material is pure parylene or has a parylene coating.

BRIEF DESCRIPTION OF THE DRAWINGS

These and other features and advantages of the present invention will be better understood by reference to the following detailed description when considered in conjunction with the accompanying drawings wherein:

FIG. 13b shows a graphical plot of data taken from pressure measurements obtained in air using the pressure sensors shown in FIG. 13a.

FIG. 14b shows a graphical plot of data taken from pressure measurements obtained in IPA using the pressure sensors shown in FIG. 14a.

FIG. 15b shows a graphical plot of data taken from pressure measurements obtained in water using the pressure sensors shown in FIG. 15a.

DETAILED DESCRIPTION OF THE INVENTION

The current invention is directed to a passive, biocompatible micromachined pressure sensor comprising a micromachined curved tube that contracts and expands in response to changes in pressure, hereinafter referred to as an "implantable sensor" or simply "sensor." The implantable sensor of the current invention is inspired by a common pressure gauge called the Bourdon tube. A Bourdon tube is a toroidal, elastic shell with thin walls, oval cross section, and with closed ends. (Schematic diagrams of a Bourdon tube are provided in FIG. 1.) As shown in FIG. 2, when such a closed flexible tube is exposed on the outside or on the inside to uniform normal wall pressure, the curvature of the center line of the tube changes proportionally with the applied wall pressure. Measurements of the resultant motion of one end of the tube with reference to the other may then be interpreted, after appropriate calibration, as pressure measurements. The current invention recognizes that micromachined Bourdon tubes and other tubular curved closed-ended structures may be used as implantable pressure sensors for IOP applications.

Figure 1:
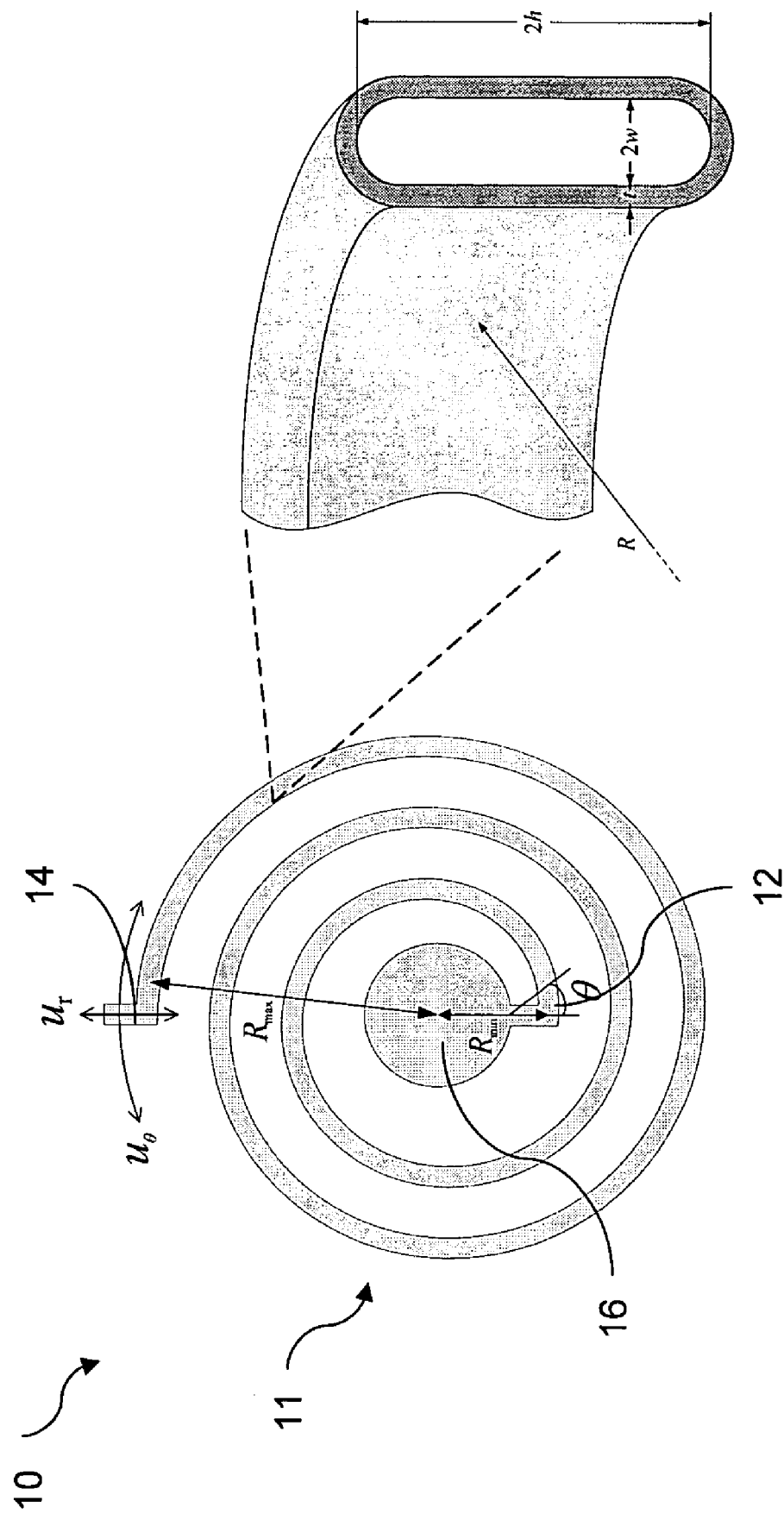
FIG. 1 provides a schematic view of a Bourdon tube sensor in accordance with one exemplary embodiment of the current invention.
Figure 2:
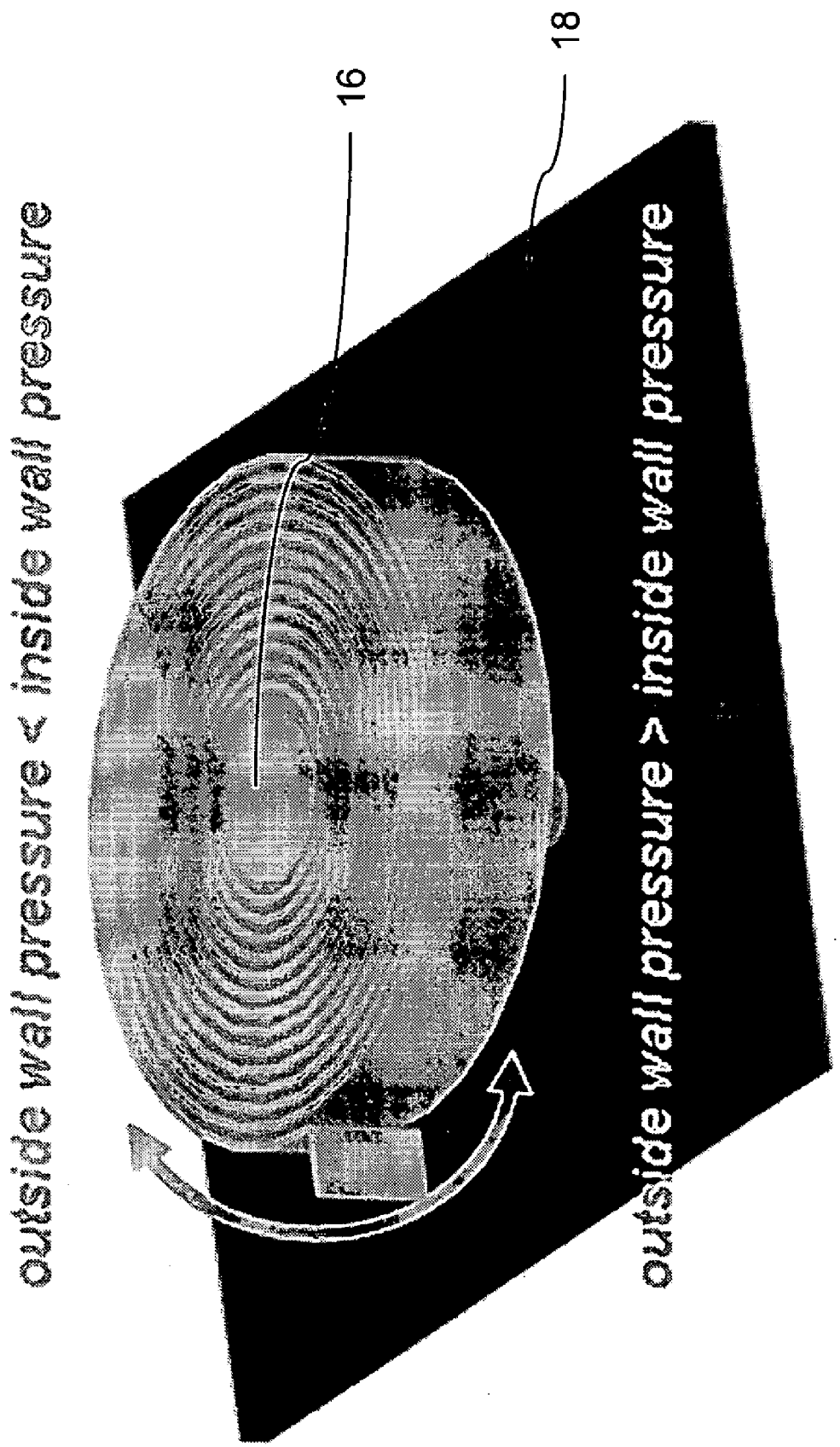
FIG. 2 provides a schematic perspective view of an intraocular pressure in accordance with the current invention and its relative motion with increasing and decreasing pressure.
Figure 3:
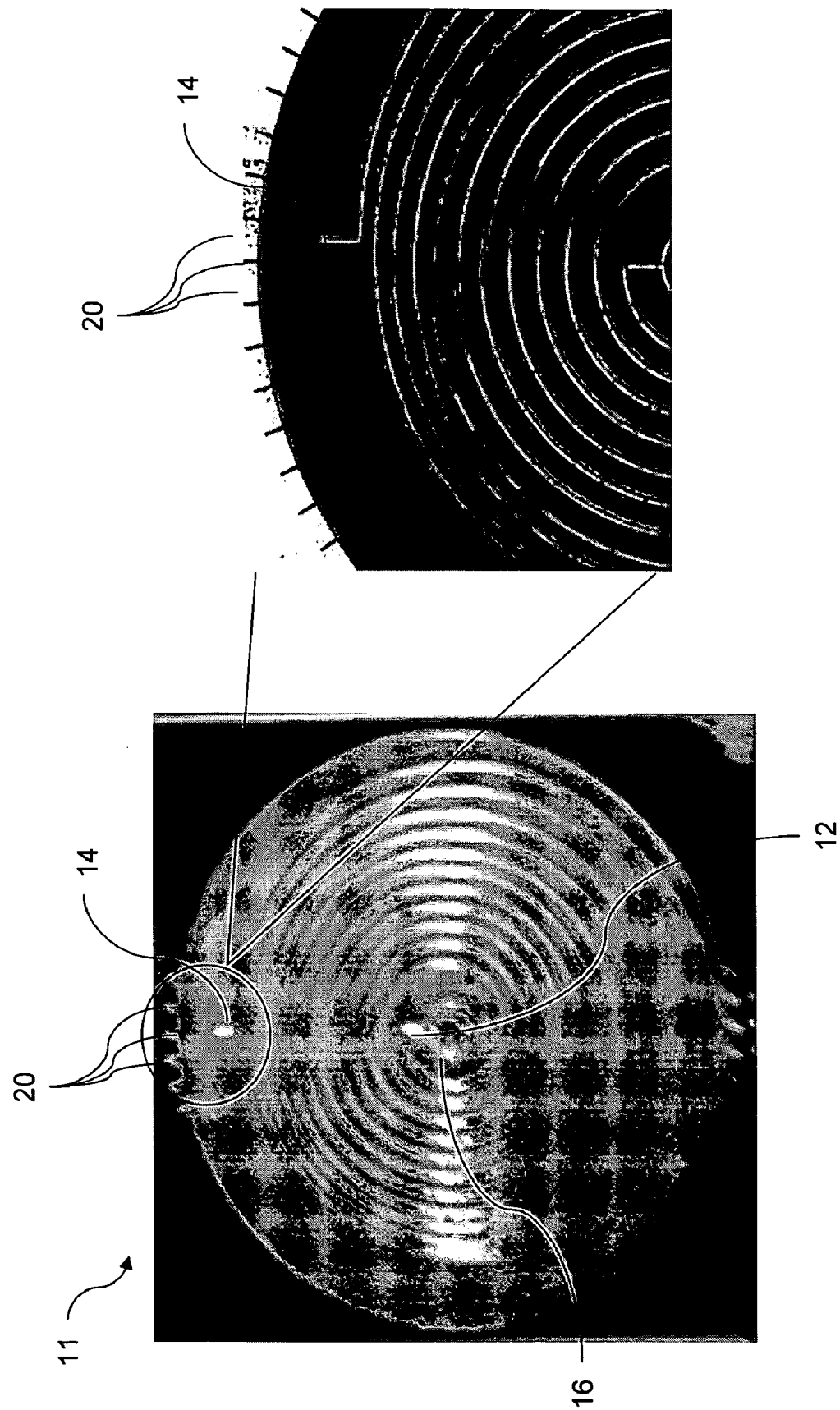
FIG. 3 shows SEM micrographs (stereoscope image in FIG. 3a and microscope image in FIG. 3b) of a micromachined sensor in accordance with one embodiment of the current invention.

As shown in FIGS. 1 and 2, in one embodiment, the sensor 10 of the current invention takes the shape of a standard Bourdon tube, i.e., a high-aspect-ratio 3-D free-standing Archimedean spiral 11, with closed ends 12 and 14. As shown best in FIG. 2, the central part of the device is a cylinder 16 fixed to a substrate 18 which also keeps the device fixed. Although not required, the device may also be provided with measurement fiducials 20 on the outside aspect to provide a more easy optical measurement of the relative motion of the outer end 14 of the sensor. In such an embodiment, the fixation of the device on the substrate is of added importance so that the end 14 of the sensor is kept in register with the fiducials 20. A micrograph of a Bourdon tube-type sensor in accordance with the current invention, including the measurement fiducials is shown in FIG. 3.

The mechanism of the sensor of the current invention relies on the phenomenon that, when the pressure inside a closed flexible bent structure that has been fixed to the surface at one end, such as the Bourdon tube shown in FIG. 2, is controlled as a constant, the pressure difference $\Delta P$ between inside and outside of the sensor imparts a bending moment to the spiral around the fixed end. This bending moment is the source of the output radial displacement $U_r$ and angular displacement $U_\theta$. Although this kind of design (Bourdon tube) has been used widely in industry, exact solutions of resultant deformations and stresses are hard to find due to the complicated hollow, toroidal shape. Present analyses are thus all based on a highly simplified and approximated calculation. See, e.g., R. A. Clark and E. Reissner, "Deformations and Stresses in Bourdon Tubes," *Journal of Applied Physics*, 21(12), 1950, pp. 1340–1341; R. Dressler, "Elastic Shell-Theory Formulation for Bourdon Tubes," *Journal of Basic Engineering*, Trans. of ASME, 87(4), 1965, pp. 1072–1077; and A. Wolf, "An Elementary Theory of the Bourdon Gage," *Journal of Applied Mechanics*, Trans. of ASME, 13(3), 1946, pp. 207–210, the disclosures of which are all incorporated herein by reference.

Among different simplified formulations, the elastic thin-shell theory presented by Wolf is applied for the following analysis of the theoretical pressure sensitivity of the sensors of the current invention. In FIG. 1, a number of dimensional characteristics are defined, these values will be used in the following analysis, where R is the varying curvature, in which $R_{max}$ and $R_{min}$ are maximum and minimum curvatures of the spiral; $\theta$ is the coiled angle of the spiral; and t, 2w, 2h are wall thickness, width, and height of the hollow elliptical structure, respectively. By applying the theory of pure bending in thin shells, the approximated sensitivity of radial deformation can be retrieved as:

$$\frac{\delta R}{R} = \frac{4}{15} \frac{\Delta P}{E} (1-v^2) \frac{h^4}{wt^3} \frac{C_1}{1 + \frac{4}{35}(1-v^2)\frac{h^4}{R^2 t^2} C_2} \quad \text{Eq. (1)}$$

in which $\Delta P$ is the pressure difference between the inside and outside of the tube, E is the Young's modulus, $\upsilon$ is Poisson's ratio, and $C_1$ and $C_2$ are constant coefficients from Table 1, below.

TABLE 1

| | Constants $C_1$ & $C_2$ | |
|---|---|---|
| w/h | $C_1$ | $C_2$ |
| 0.0 | 1.000 | 1.000 |
| 0.1 | 1.273 | 1.040 |
| 0.2 | 1.469 | 1.059 |
| 0.3 | 1.574 | 1.057 |
| 0.4 | 1.574 | 1.024 |

In turn, the radial displacement of the sensor arm is given by:

$$u_r = \left[\frac{\delta R}{R}\right]_{R_{max}} \quad \text{Eq. (2)}$$

$$R_{max} = \left(\frac{4C_1}{15}\frac{\Delta P}{E}(1-v^2)\frac{h^4}{wt^3}\right)\frac{R_{max}^3}{R_{max}^2 + \frac{4}{35}(1-v^2)\frac{h^4}{t^2}C_2}$$

And the angular displacement of the sensor arm is given by:

$$u_\theta = \left(\frac{4C_1}{15}\frac{\Delta P}{E}(1-v^2)\frac{h^4}{wt^3}\frac{\theta_{total}}{R_{max}}\right)\left[R^2 - D\log(\sqrt{R^2+D})\right]_{R_{min}}^{R_{max}} \quad \text{Eq. (3)}$$

(in meters)

$$\approx \left(\frac{48}{\pi}C_1\frac{\Delta P}{E}(1-v^2)\frac{h^4}{wt^3}\frac{\theta_{total}}{R_{max}^2}\right)\left[R^2 - D\log(\sqrt{R^2+D})\right]_{R_{min}}^{R_{max}} \quad \text{Eq. (4)}$$

(in degrees)

$$\text{with: } D = \frac{4}{35}(1-v^2)\frac{h^4}{t^2}C_2 \quad \text{Eq. (5)}$$

Figure 4A:
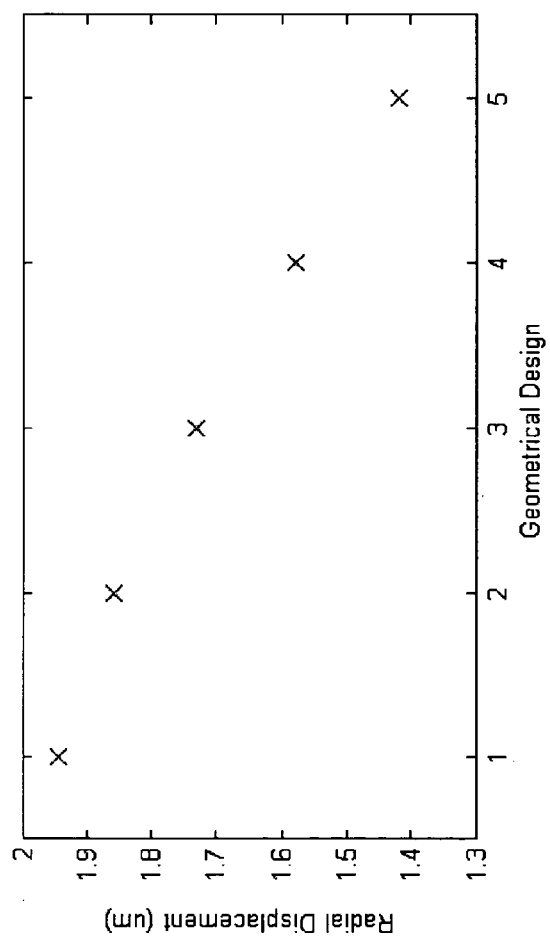
FIGS. 4a to 4c provide graphical plots of data on the relative motion of exemplary embodiments of intraocular pressure sensors in accordance with the current invention under changing pressure conditions.
Figure 4B:
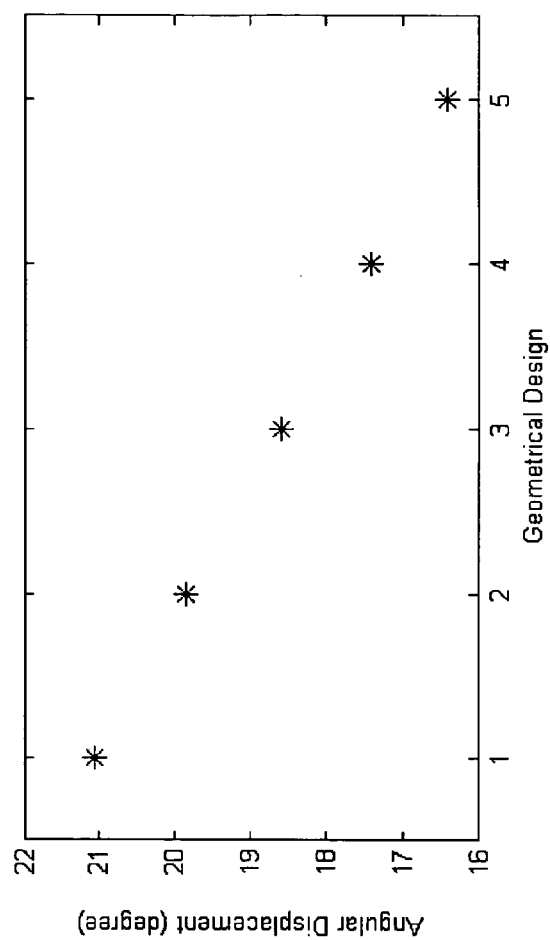
Figure 4C:
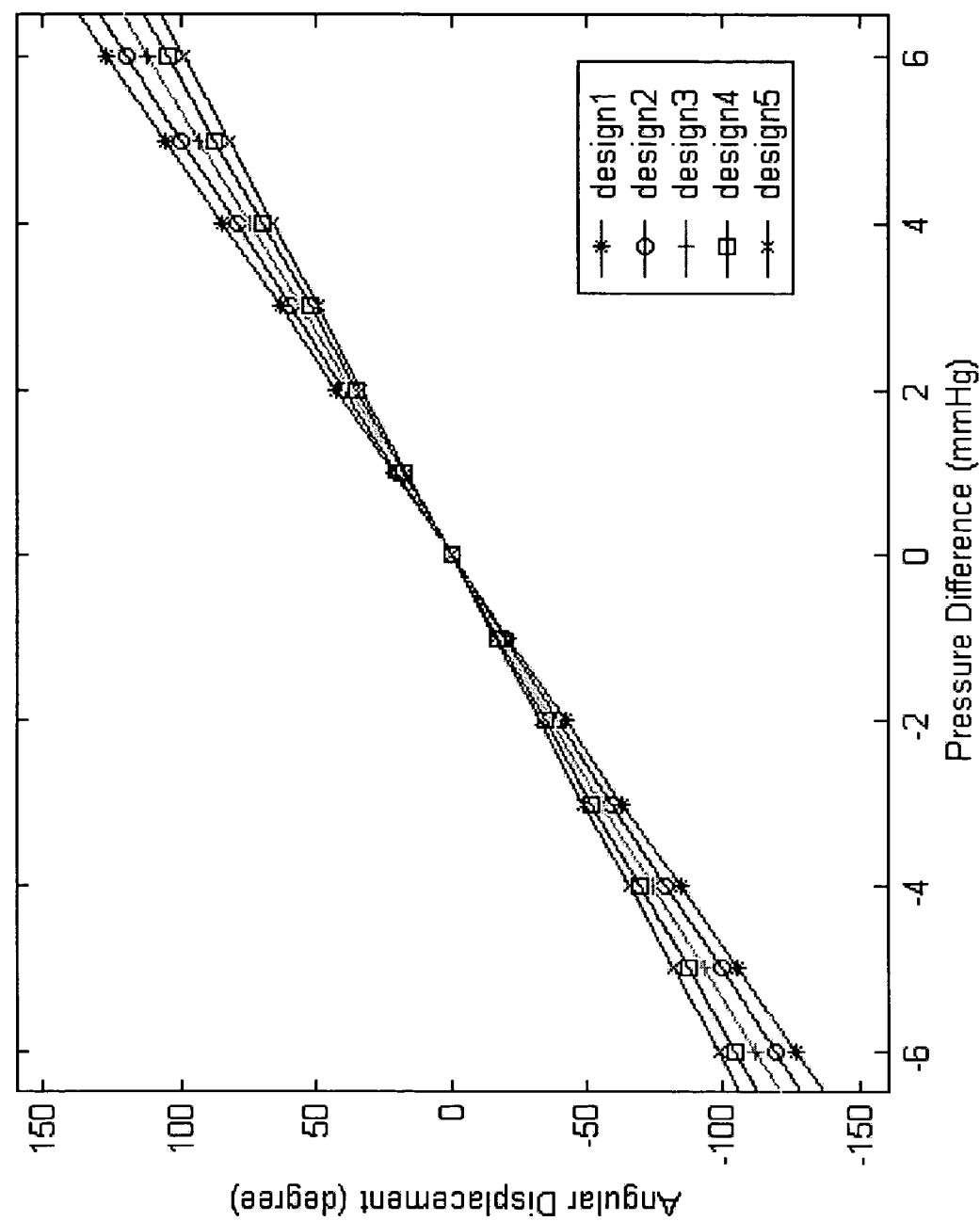
Figure 5C:
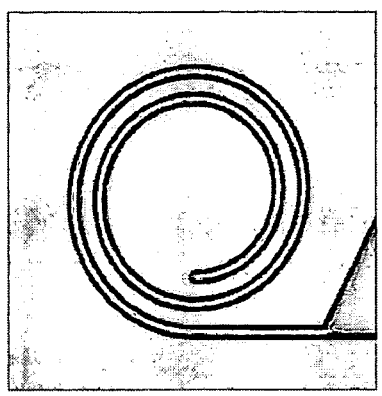
FIGS. 5a to 5f show microscope micrographs of various bent tube configurations for pressure sensors in accordance with additional embodiments of the current invention.
Figure 5F:
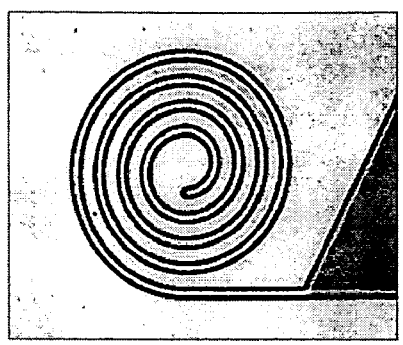
Figure 5B:
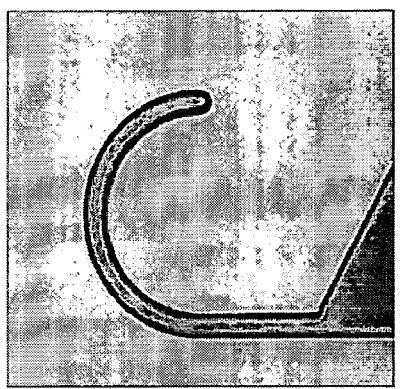
Figure 5E:
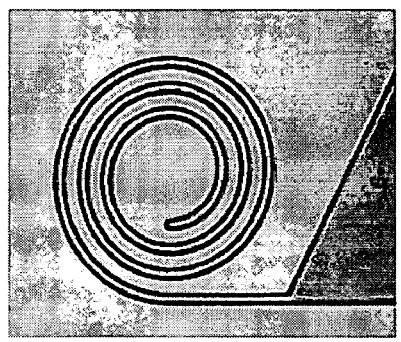
Figure 5A:
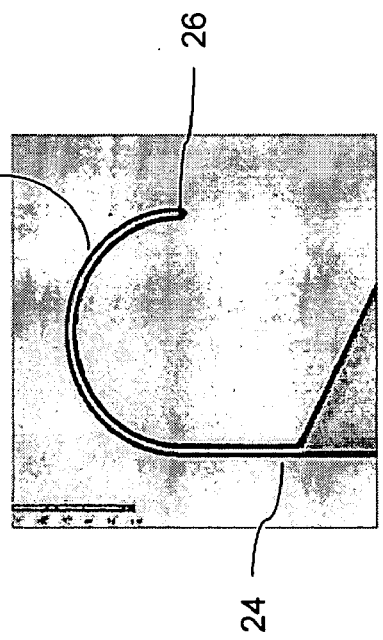
Figure 5D:
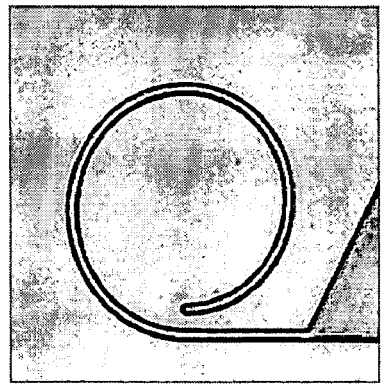

Table 2, below summarize the theoretical results for resolving a 1 mmHg (133.32 Pa) pressure difference using several different designs of sensors incorporating Bourdon tubes having different critical dimensions. Some of the geometrical features are intentionally chosen to indicate the limitations of the state-of-the-art micromachining process. The sensitivity of the various design and the control of the level of displacement are also plotted in FIGS. 4a to 4c, which show the $U_r$ for a 1 mmHg pressure difference (4a), the $U_\theta$ for a 1 mmHg pressure difference (4b), and $\Delta P$–$U_\theta$ (4c), respectively. As shown, simply varying the relative dimensions of the body of the sensor can be used to tune the sensitivity of the sensor, and the size of the indicating displacement of the sensor of the current invention.

TABLE 2

Theoretical Results for Various Sensor Designs

| | design1 | design2 | design3 | design4 | design5 |
|---|---|---|---|---|---|
| t | 1 μm | 2 μm | 3 μm | 4 μm | 5 μm |
| 2w | 2 μm | 4 μm | 6 μm | 8 μm | 10 μm |
| 2h* | 40 μm | 80 μm | 120 μm | 160 μm | 200 μm |
| $R_{min}$ | 100 μm | 100 μm | 100 μm | 100 μm | 100 μm |
| $R_{max}$ | 1000 μm | 1000 μm | 1000 μm | 1000 μm | 1000 μm |
| coiled turns** | 35 | 35 | 35 | 35 | 35 |
| $u_r$ | 1.944 μm | 1.858 μm | 1.731 μm | 1.579 μm | 1.419 μm |
| $u_\theta$ | 21.054° | 19.859° | 18.589° | 17.415° | 16.393° |

*determined mostly by the high-aspect-ratio DRIE process
**the total spiral angle $\theta_{total}$ = (coiled turns) * 360°

It should be understood that although only Bourdon-type sensors are discussed above, the same principals of operation, critical dimensions, and theoretical calculations can be applied to any closed hollow structure having a curved body that serves as a fixed moment arm. For example, FIGS. 5a to 5f show a variety of bent close-ended hollow bodies that could be utilized as pressure sensors in the current invention. These vary from simple hook designs (5a) to full spiral tubes (5f). These embodiments are provided to emphasize that the number and type of turns is not critical to the operation of the current invention. In addition, as shown the fixed end of the sensor need not be located central to the curved body, but can also be located at the outer end of the curved body such that the movement occurs in the interior of the sensor body. In such an embodiment, only the technique for measuring the motion of the sensor body relative to the substrate would need to be altered. In short, the only requirements are at least one bent flexible portion of a tube 22 having two closed ends, a first end fixed to a substrate 24 and a second end 26, which is free to move in response to a pressure change.

Figure 6B:
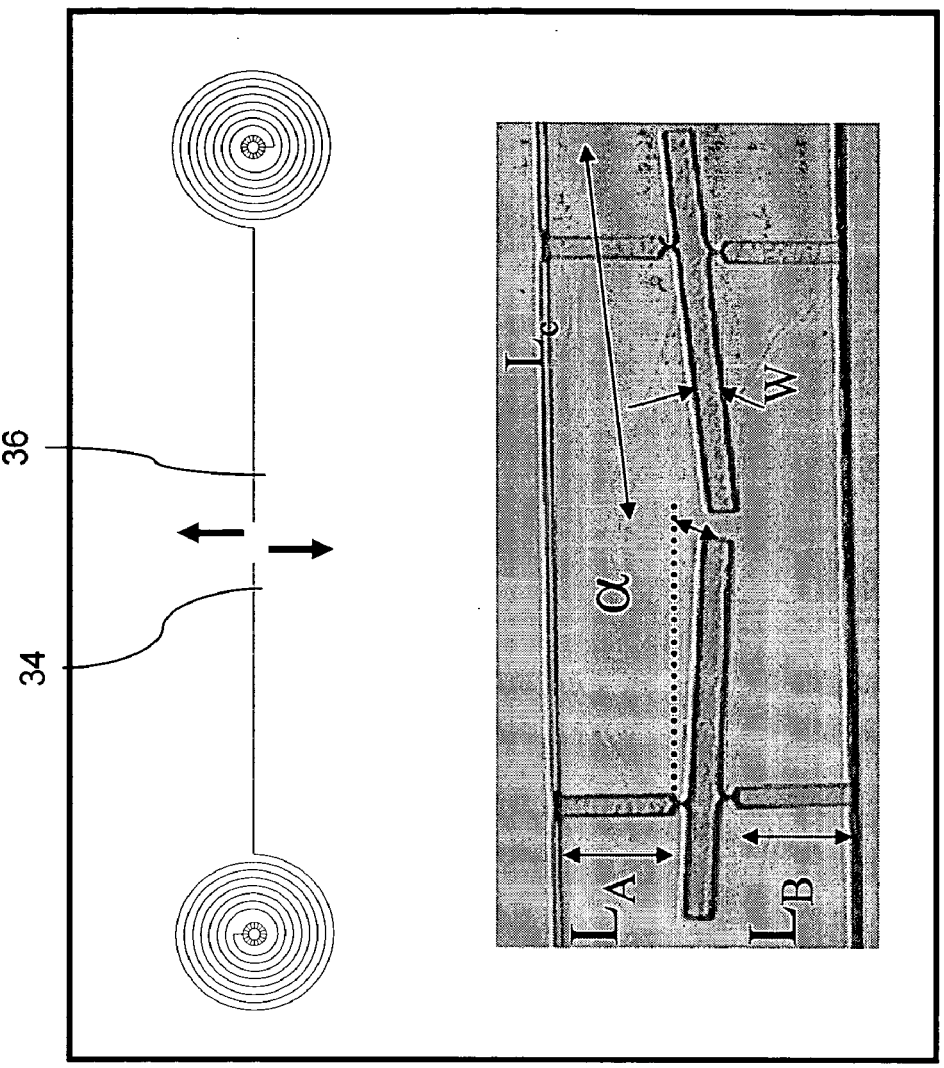
FIGS. 6a and 6b show schematic diagrams of spiral-type pressure sensors having large moment arms in accordance with another embodiment of the current invention.
Figure 6A:
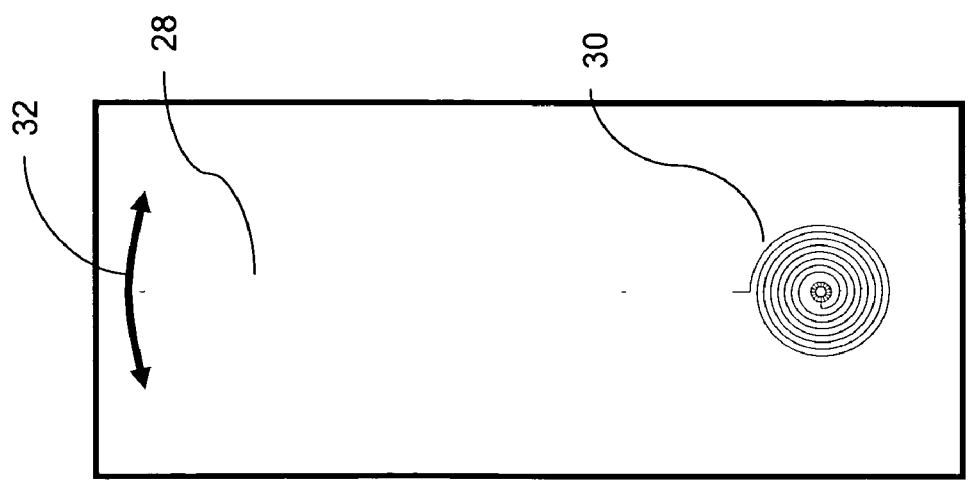

Further, as shown in FIGS. 6a and 6b other modifications to the sensor may be made, such as lengthening the indicator portion 28 at the free end of the sensor body 30 such that even minor movements of the bent tube produce very large displacements at the far end 32 of the sensor body. Likewise, as shown in FIG. 6b, an even more sensitive arrangement would involve the disposition of two of the extended sensors of FIG. 6a in opposition to one another, such that the two indicator portions 34 and 36 would move in opposite directions one from the other in response to a pressure change, effectively doubling the sensitivity of the single extended arm pressure sensor of FIG. 6a. An SEM micrograph of such an opposing tip sensor formed in accordance with the current invention is provided in the inset to FIG. 6b.

Figure 7B:
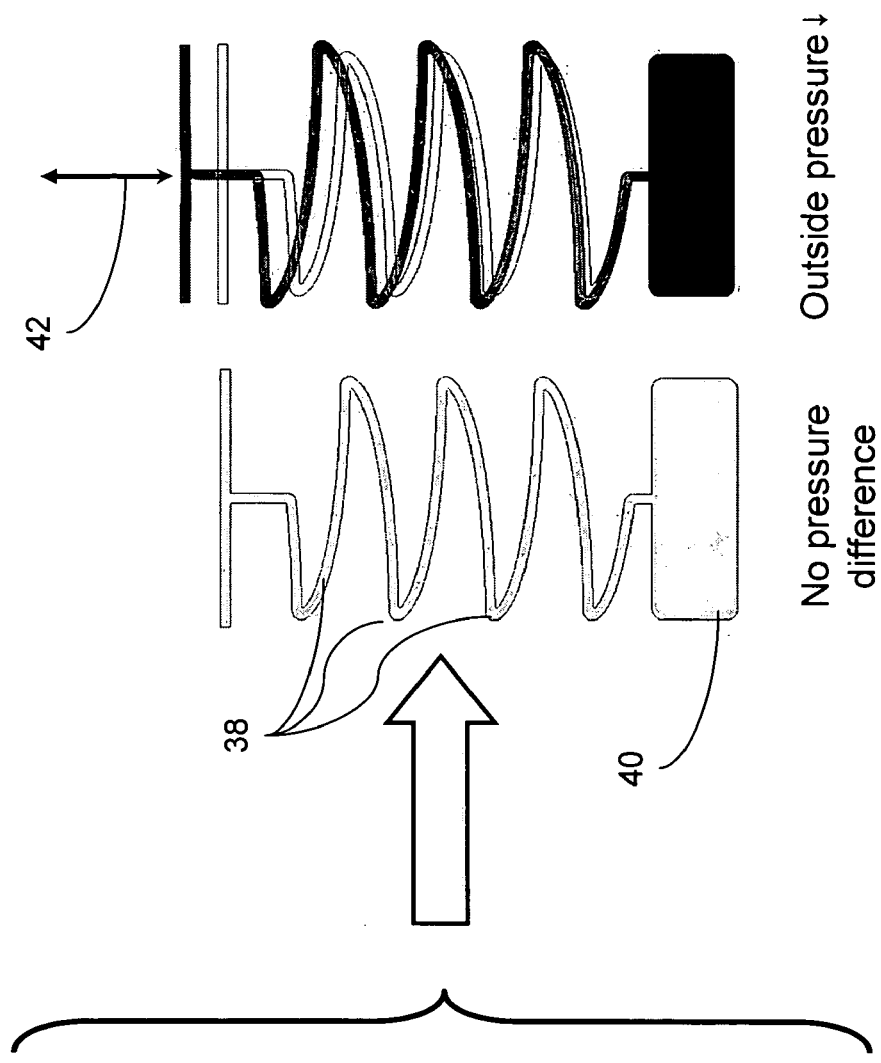
FIGS. 7a and 7b show schematic diagrams of a compact linear-type pressure sensor in accordance with another embodiment of the current invention.
Figure 7A:
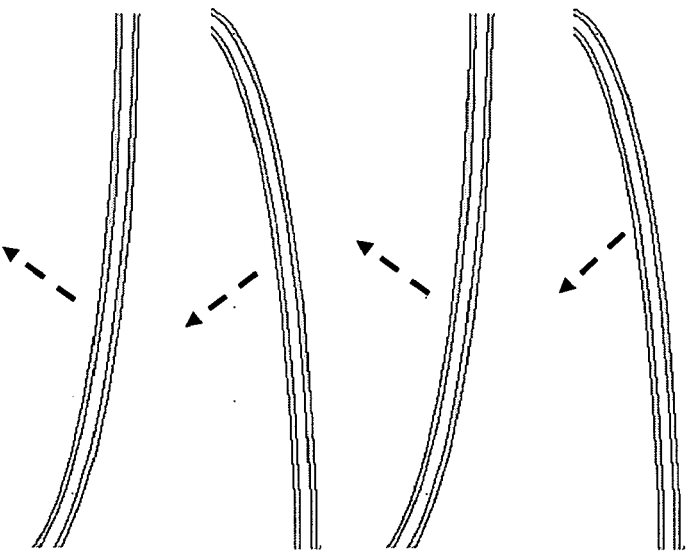

Finally, although only rotational motion sensors arrangements are discussed above, it should be understood that other arrangements of pressure sensitive constructs are contemplated by the current invention. For example, in one embodiment of the invention shown schematically in FIGS. 7a and 7b, a series of curved section 38 arranged and joined end to end in a zigzag fashion. In this embodiment one end of the curved section at one end of the zigzag structure is fixed to the substrate 40 and the remaining sections are free to move, such that a change in pressure imparts a linear motion 42 in the series of bent tubes (see, e.g., FIG. 7b).

It should also be understood that although only a single sensor is shown in each of the embodiments discussed above, multiple sensors or large arrays of sensors could be provided on a single substrate to provide verification and back-up sensors. In addition, although only simple rectangular or square planar substrates are shown in the embodiments discussed above, it should be understood that the support or substrate for the sensors of the current invention can take any suitable form.

The above embodiments are not meant to provide a definitive list of possible sensor designs. The concept of the device is based on a Bourdon tube, but only requires that the pressure inside a hollow bent body is sealed at a designated constant, such that when a uniform pressure difference is generated across the channel walls, a bending moment is created in opposition to a fixed end of the body that in turn forces an in-plane radial and angular deformation of the hollow body. The deformation, which can be visualized by movement of the free end of the hollow body, is linearly related to the pressure difference. Therefore, the corresponding environmental (outside-wall) pressure can be measured. The remaining aspects of the geometry depend principally on design considerations, such as preventing out-of-plane deformation, and the sensitivity required for the desired application. For example, the angular deformation indicated by the tip rotation can be amplified by increasing the number of coiled turns or increasing the length of the indicator arm of the free tip. In addition, as discussed above, a channel structure with thinner walls and higher aspect-ratio profile is more sensitive to environmental pressure change. In any application, each of these design factors must be considered to achieve the desired pressure sensitivity of the device.

Figure 8:
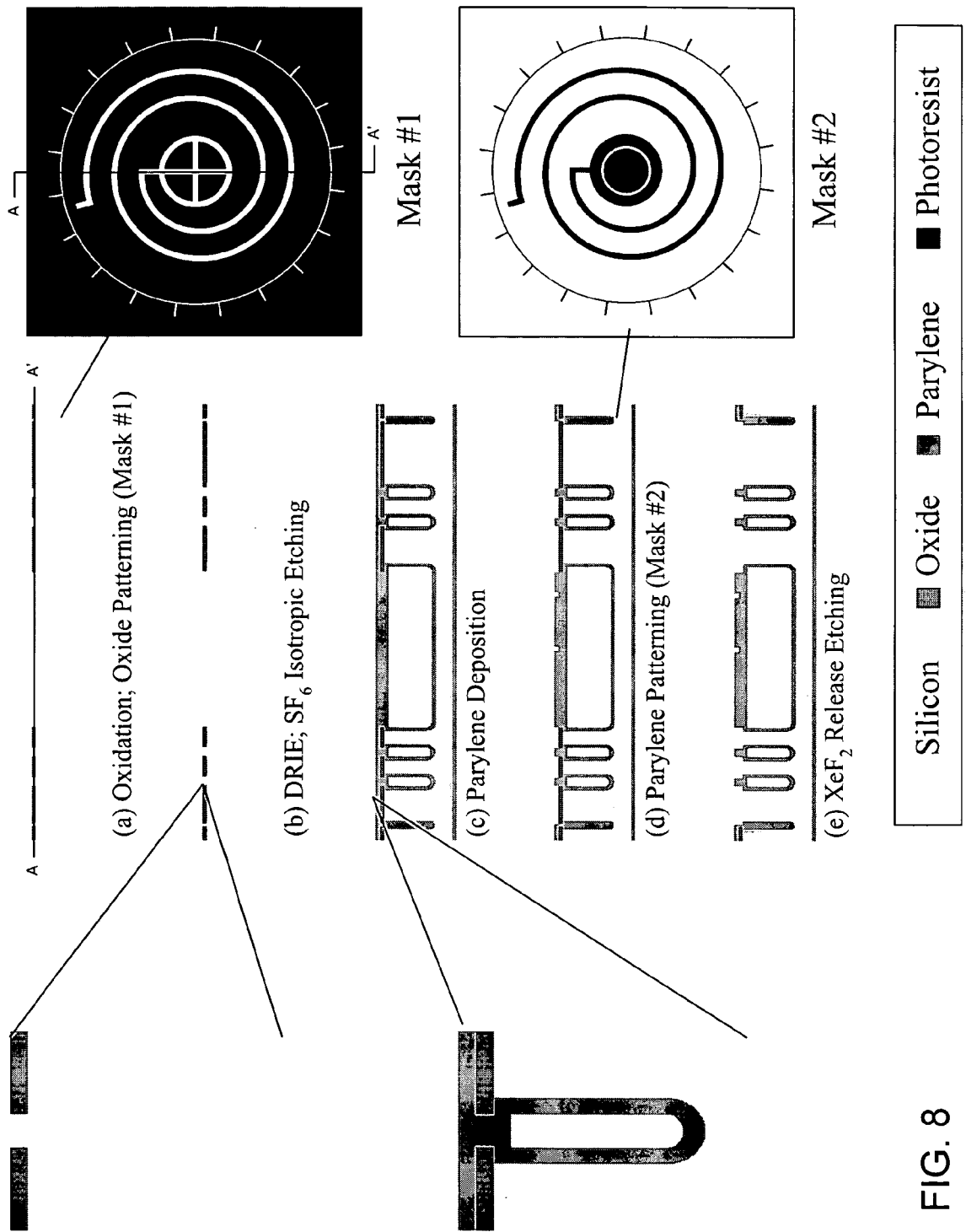
FIG. 8 shows a schematic diagram of the process flow for an embodiment of a method for manufacturing the pressure sensor of the current invention.
Figure 9B:
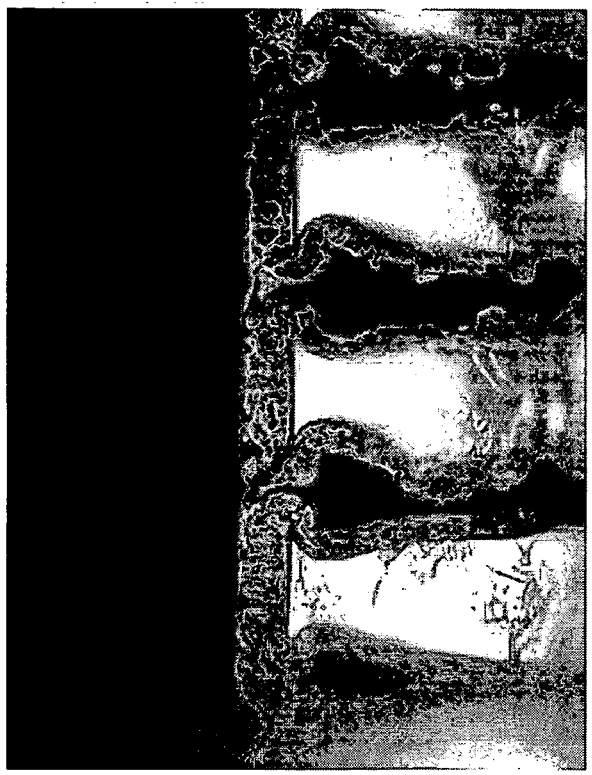
FIGS. 9a and 9b show microscope micrographs of trenches at different stages of formation in accordance with the method of the current invention.
Figure 9A:
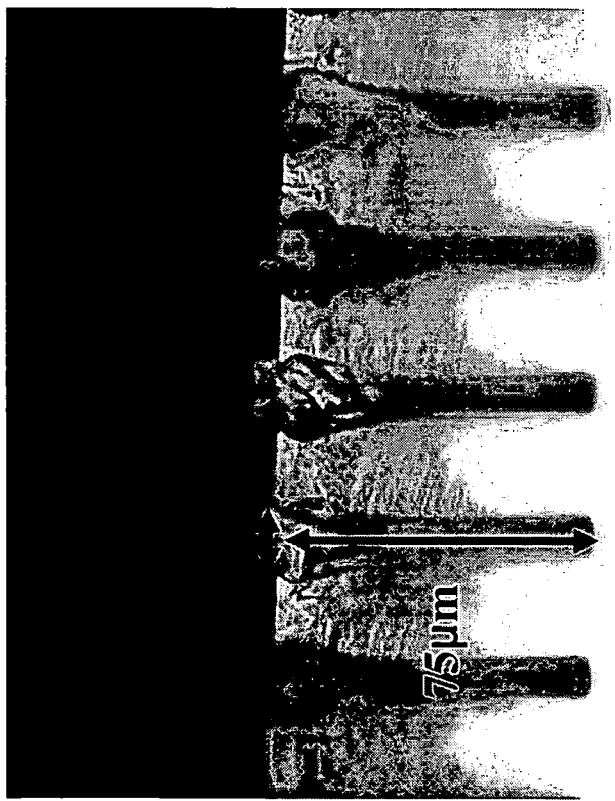

Although only devices have been discussed thus far, the current invention is also direct to methods of manufacturing the pressure sensors of the current invention. FIG. 8 shows a schematic flow-chart for one exemplary manufacturing method, FIGS. 9*a* and 9*b* shown SEM micrographs of cross-sections of the hollow body made in accordance with the current invention during various stages of the process.

As shown, the fabrication process begins with 5000 Å wet oxidation on a standard silicon wafer (8*a*). After patterning the oxide (see inset of FIG. 8*a*), a conventional Bosch process in a PlasmaTherm DRIE is used to etch trenches (8*b*). $SF_6$ plasma etching is then performed to isotropically undercut the silicon surrounding the trenches. 75 μm deep, 6 μm wide trenches with 2.5 μm sidewall undercut can be created by using the above process (see inset to FIG. 8*b* and microscope micrograph of FIG. 9*a*). Before parylene deposition, a short $C_4F_8$ deposition is performed to intentionally degrade the adhesion between the silicon and the parylene. Subsequently a 5 μm thick parylene layer is deposited (8*c*). This conformal deposition concurrently seals the trenches to form the spiral channel (see inset to FIG. 8*d* and microscope micrograph of FIG. 9*b*), the pointing tip, the surrounding indicators, and a parylene "web" structure at the center that supports the channel. The parylene is then patterned by using oxygen plasma (8*d* and see inset of FIG. 8*d*). During this step, a thin opening ring is created in the center to prevent the complete sealing of the device. Finally, after photoresist and oxide removal, the spiral channel is released from the substrate by $XeF_2$ gaseous etching (8*e*).

Figure 10:
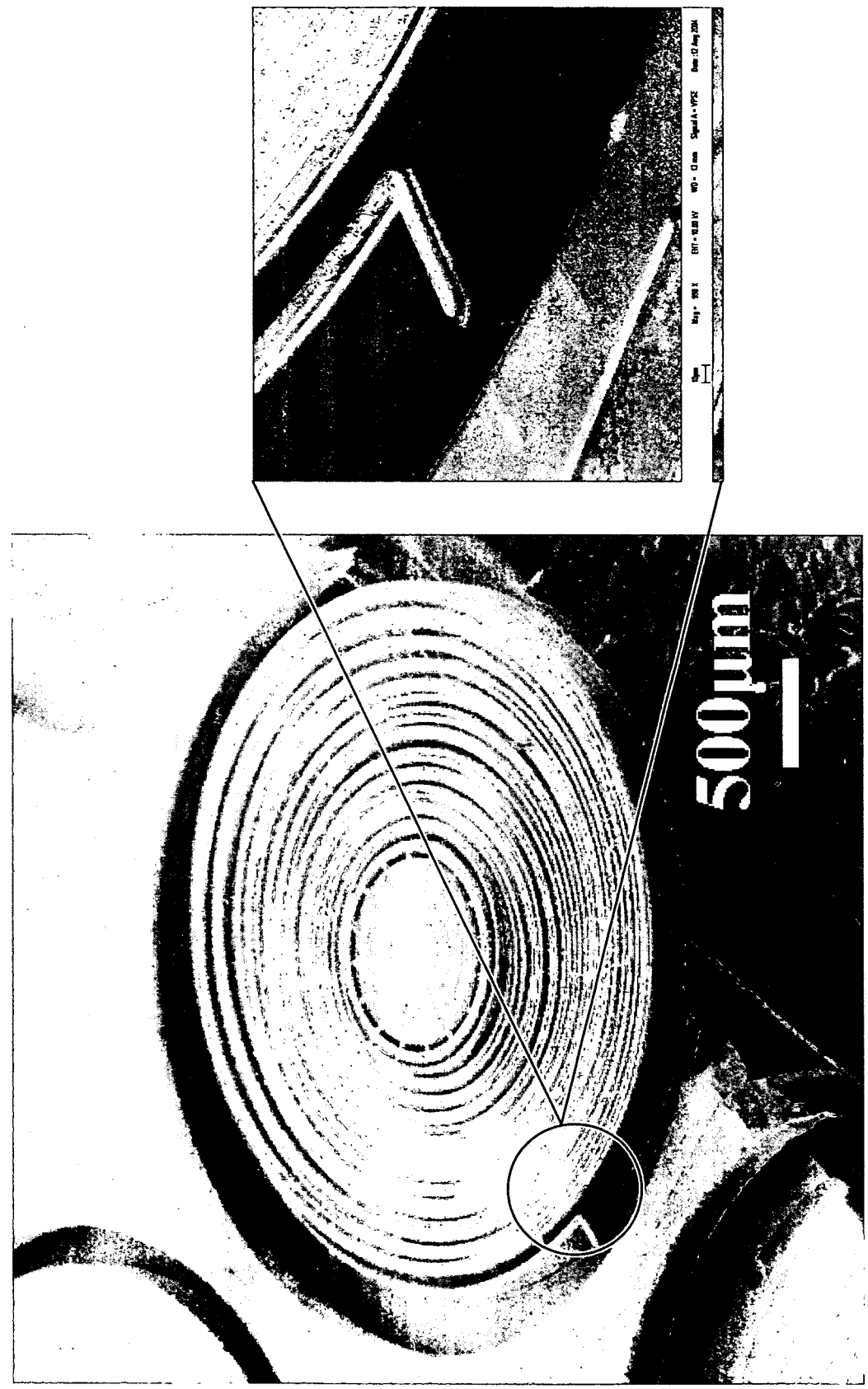
FIG. 10 shows an microscope micrograph of a pressure sensor formed in accordance with the method of the current invention.

A fabricated device with a radius of 1 mm is shown in FIG. 10. The radius of the central supporting cylinder is 100 μm. The spiral channel ends at a 100 μm long, 6 μm wide pointing tip (shown in detail in the inset to FIG. 10), and the rotation angle can be optically recorded from 5 degree/division indicators surrounding the device. Because the sensor device is still open to environmental pressure, a photoresist drop is dispensed over the central cylinder and dried to seal the channel at a controllable pressure. At the current phase of development, the device is sealed at 1 atm as the gauge reference.

Figure 11B:
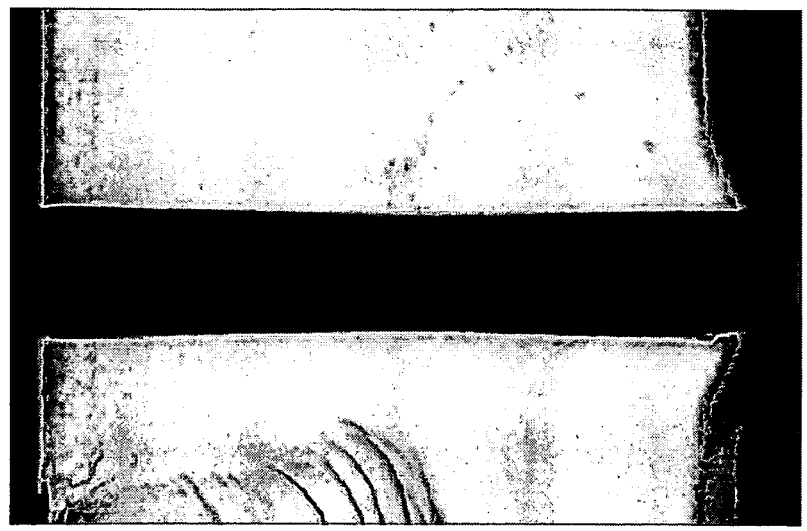
FIGS. 11a and 11b provide microscope micrographs showing details of trenches formed in accordance with the methods of the current invention.
Figure 11A:
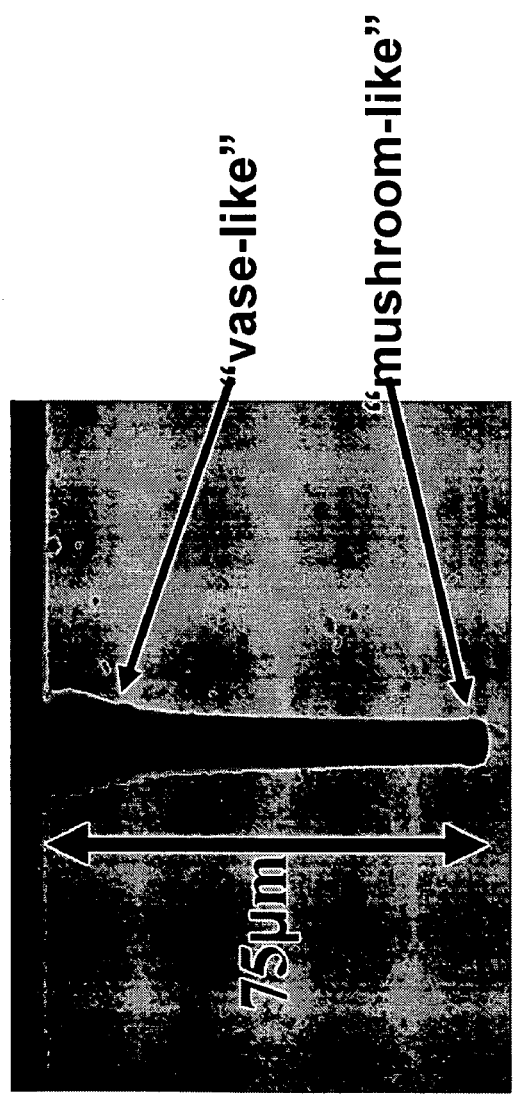

Ideally, the undercut surrounding the etched trenches should be isotropic. The physical motion of the reactive ions in plasma, however, leads the $SF_6$ plasma to first create a "mushroom-like" profile at the bottom of trenches, and as the etching time increases, the trench sidewalls are etched in a "vase-like" profile instead of a uniform one (see SEM in FIG. 11*a*). This phenomenon is more obvious in higher aspect-ratio trenches. In order to create a better profile for greater pressure responses of the spiral channel, a modified DRIE may be used in which SF6 is used to undercut/compensate the trench, but then an oxygen plasma is used to clean surplus $C_4F_8$ to avoid the effects created by the excess reactive ions in the plasma.

Another issue is that the released spirals are vulnerable to outside variation, such as fluid flow, vibration, and electrostatic attraction. These environmental changes can cause the sensor body to move sideways to contact other structures or to unwind out of plane. As a result, the sensor may be disposed within a depression on the substrate, as shown in FIG. 10 to provide a more robust structural design or with additional supporting structures.

In summary one embodiment of a method of forming a pressure sensor in accordance with the current invention involves the following steps:
1) wet oxidation of silicon wafer;
2) spin-on photoresist, expose, and develop;
3) Pattern transfer using buffered oxide etch;
4) DRIE: standard Bosch process;
5) $SF_6$ etching for isotropic undercut;
6) double-sided parylene coating;
7) spin-on photoresist, expose, and develop;
8) Parylene etch using oxygen plasma;
9) photoresist removal;
10) Oxide removal; and
11) Silicon release etch (such as $XeF_2$ gaseous etching, $SF_6$ plasma etching, and HNA wet etching).

Although any suitable material can be used to manufacture the sensors of the current invention, in one preferred embodiment, a biocompatible material such as parylene (poly-para-xylylene) is selected. Parylene is an ideal structural material for implantable sensors because of its desirable properties, such as high flexibility (Young modulus ~3 GPa), chemical inertness, and biocompatibility. Moreover, parylene is compatible with microfabrication technology and can be deposited as a pinhole-free conformal coating at room temperature. It has been widely used in microfluidic and bioMEMS devices. Recently, the micromachining techniques and applications of high-aspect-ratio parylene structures have been successfully demonstrated. It should be understood that any suitable parylene material could be used such as parylene C, parylene N, parylene D, parylene F, parylene A, parylene AM, and parylene HT.

Finally, although the above discussion has focused on the construction and structure of the basic microstructure, it should be understood that a device such including the pressure sensor according to the invention may also include a body, and any additional machinery or circuitry necessary for the device's operation. For example, the body of the pressure sensor itself can be made of any material suitable for micromachining utilizing standard lithographic or MEMS techniques to enclose the microstructure, such as, for example, aluminum, silicon, or silicon dioxide. In a preferred embodiment, the body further comprises a cap layer, which can be of any design, such that the cap layer protects the sensor from unwanted contact with the external environment. Such a cap layer could be made of any suitable material, such as, for example, a polymer (including but not limited to parylene, PDMS, or polyimide), aluminum, silicon dioxide, or silicon. Such a cap layer could be formed by any conventional MEMS process, such as growth or deposition over a sacrificial layer (not shown) deposited to encapsulate the pressure sensor wherein the sacrificial layer can subsequently be removed to expose the sensor itself. Alternatively, these support structures could be formed in a single deposition step with the pressure sensor. In a more preferred embodiment, one of the substrate, the cap layer, or walls of the sensor is transparent such that the optical source can be used to interrogate the sensor.

EXAMPLES

Figure 12:
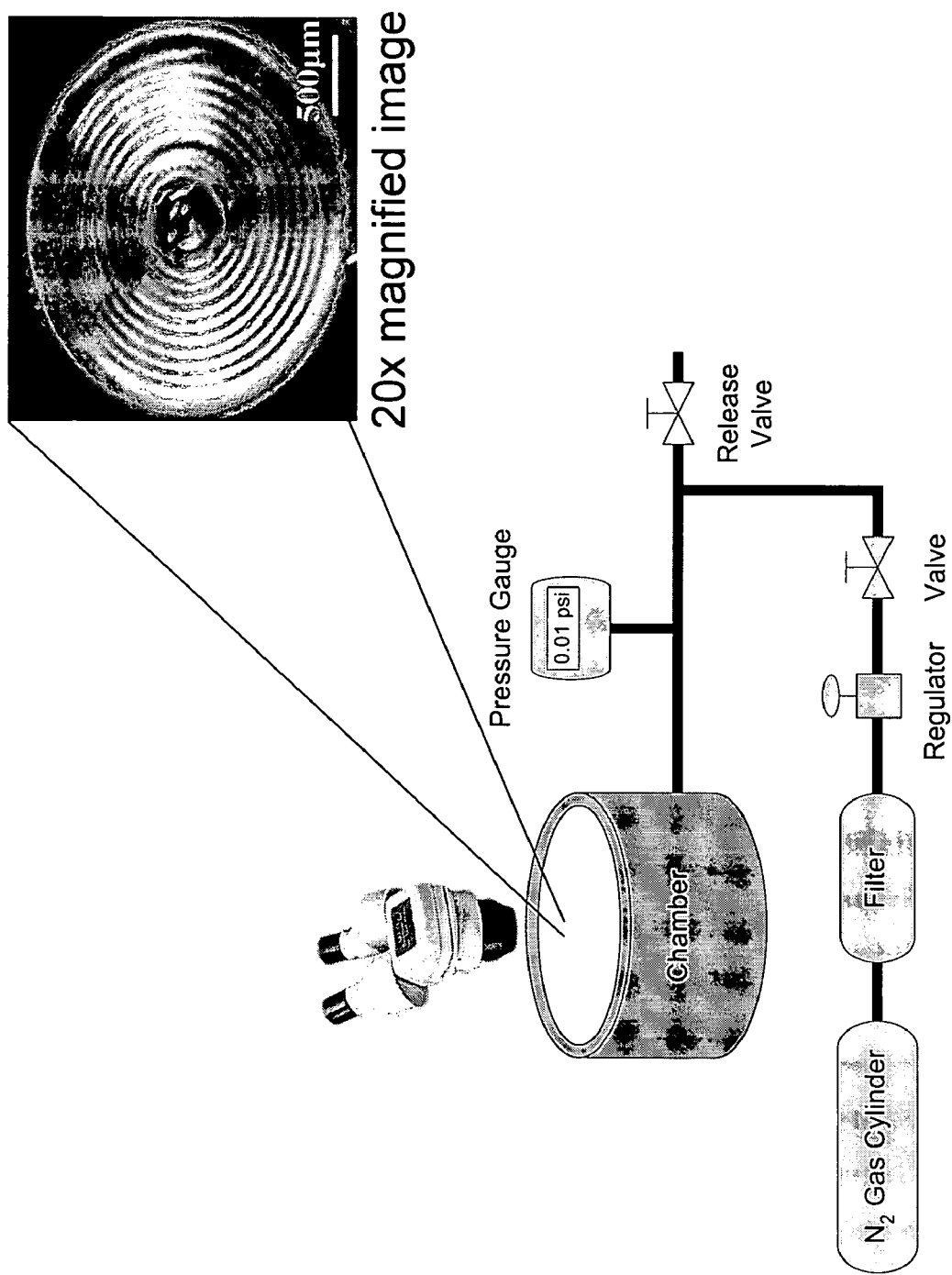
FIG. 12 shows a schematic of a measurement apparatus for use with the current invention.

The invention can be better understood with reference to the following non-limiting examples. The testing setup used in the following examples is illustrated in FIG. 12. A system consisting of an $N_2$ gas cylinder, a particle filter, an Airtrol R-800-60 pressure regulator, and two needle valves is used to regulate the pressure. One needle valve releases the applied pressure after each measurement. This system is connected to a closed chamber to provide different positive-applied pressures. The cap of the chamber is transparent to facilitate external optical observation. A device with a 10-turn spiral is placed inside the chamber and tested (inset to FIG. 12). When a pressure difference is applied between the outside and the inside of the channel, the pointing tip starts to rotate. This behavior is monitored through a stereoscope with 20× magnification and a mounted CCD camera to capture the image. Along with the optical readout, an OMEGA PCL100-30 pressure calibrator is also used to measure the real-time numerical pressure. These two readouts are analyzed to characterize the performance of the device.

Figure 13B:
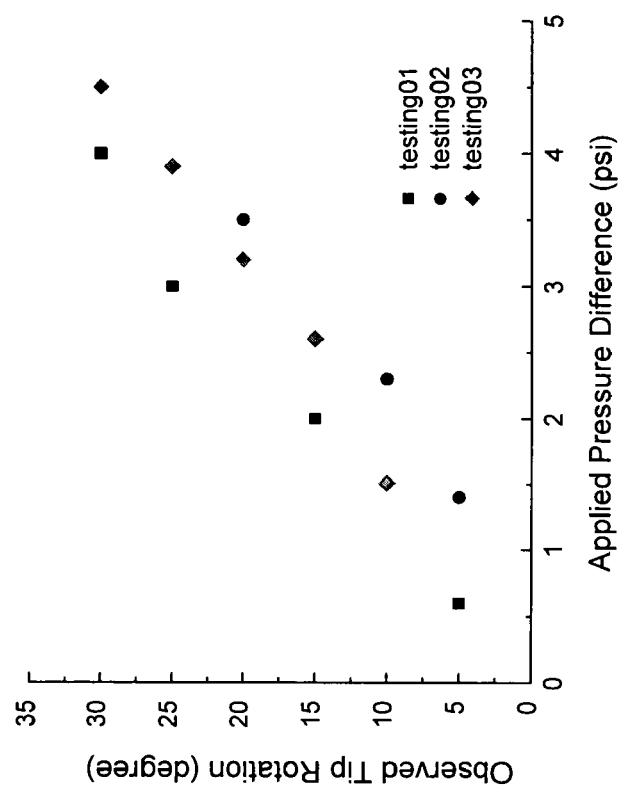
Figure 13A:
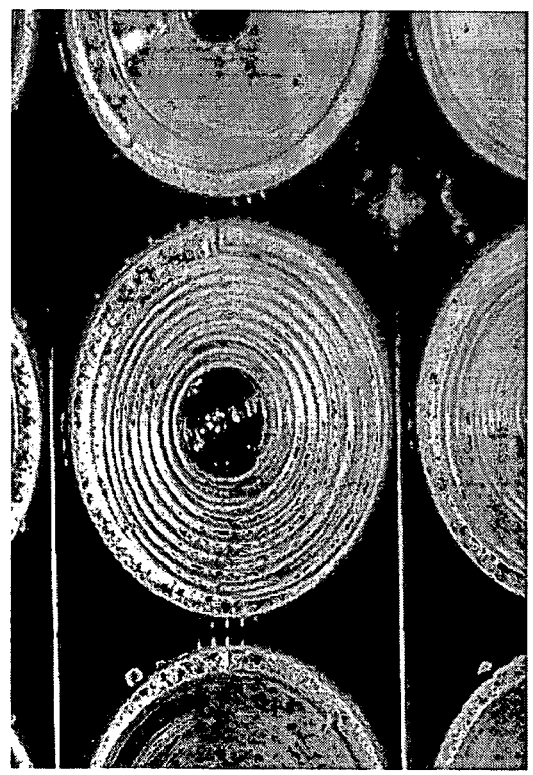
FIG. 13a shows a stereoscope micrograph of an array of pressure sensors formed in accordance with the current invention for operation in air.
Figure 14A:
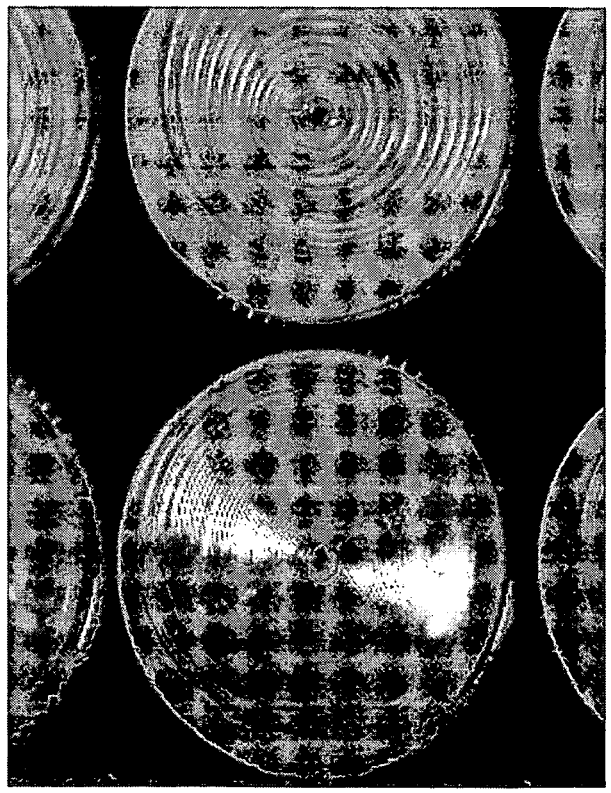
FIG. 14a shows a microscope micrograph of an array of pressure sensors formed in accordance with the current invention for operation in IPA.
Figure 14B:
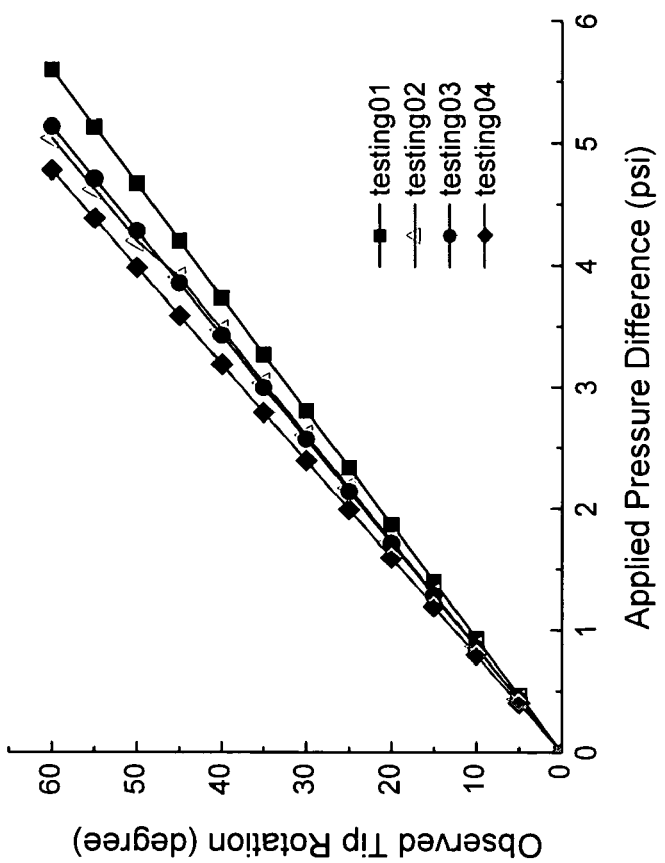
Figure 15B:
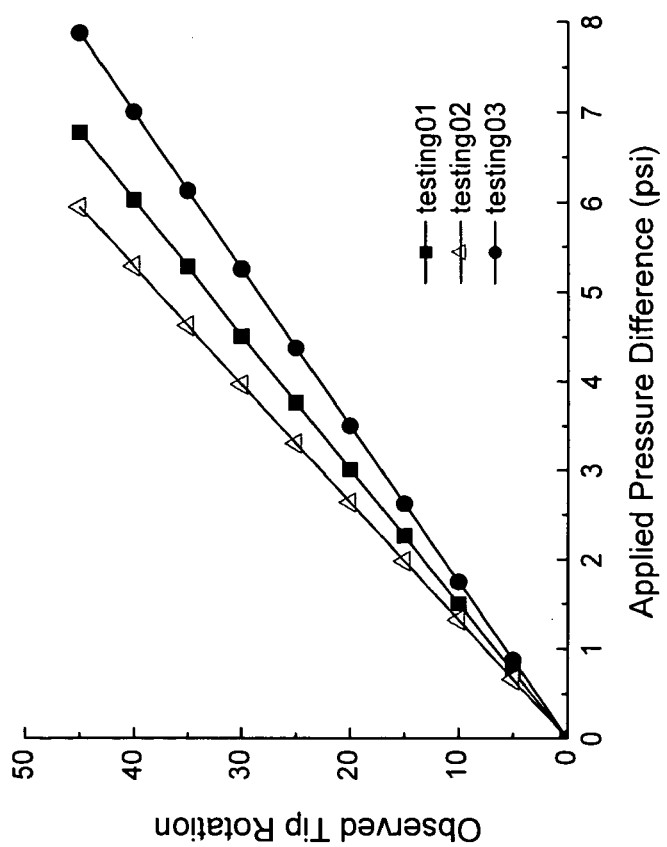
Figure 15A:
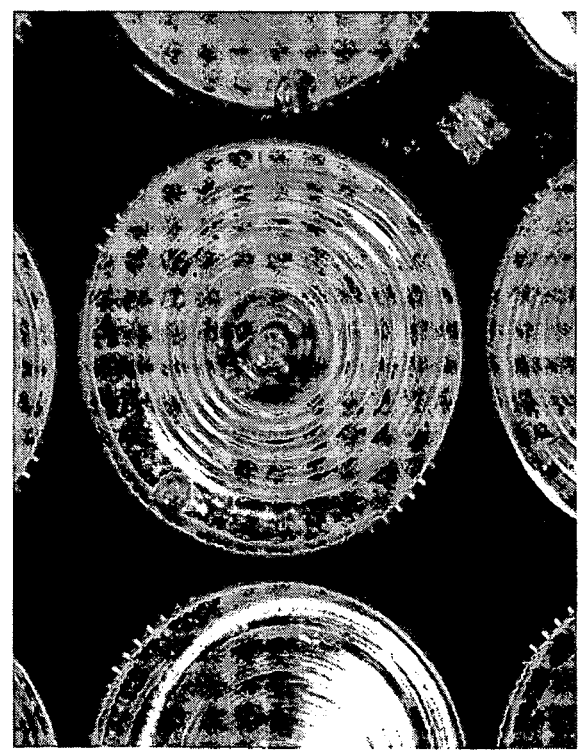
FIG. 15a shows a microscope micrograph of an array of pressure sensors formed in accordance with the current invention for operation in water.

The device was then tested in various media (e.g., air (FIG. 13), IPA (FIG. 14), and water (FIG. 15)) to accomplish feasibility and performance testing. For air, the pressure-rotation relationship is plotted in FIG. 13b. It was found that, the tip rotation does increase when the pressure difference increases, and their relationship can be fitted well to a linear curve. Likewise, the resulting pressure-rotation relationship of the sensor of the current invention in isopropyl alcohol (IPA) is plotted in FIG. 14b, and remains a linear response. Under this condition, tip rotation is continuous with pressure changes, and the sensitivity in IPA is also improved from that in air. In the pressure range of 6 psi, the measured sensitivity has an average of 0.22 degree/mmHg, with ±9% variation in specific rotation angles. Finally, the sensor of the current invention was also stested in water, which is most comparable to the saline medium of interest in IOP sensing applications. When first immersed in water, the device was not functional because the hydrophobic parylene surface induces formation of bubbles on the surface of device. Thus, when the pressure is above a certain value, some bubbles break and can cause serious deformation of the spiral because of the high surface tension of the water. This problem was solved by appropriate surface treatment in oxygen plasma, as discussed further in, T.-J. Yao, "Parylene for MEMS Applications," *Ph.D. dissertation, California Institute of Technology*, 2002, the disclosure of which is incorporated herein by reference. The spiral can be modified to be more hydrophilic, which reduces bubbling and enables use of the device in water. With the treatment, the device becomes operational in aqueous environments. For example, a pressure-rotation plot of the sensor according to the current invention is shown in FIG. 15b. The measured sensitivity is 0.13 degree/mmHg with ±15% variation.

The above experiments demonstrate that a mechanical passive micromachined pressure sensor can be successfully fabricated with as low as 0.13 degree/mmHg sensitivity. The passive pressure-driven rotation in a high-aspect-ratio tube can also facilitate a direct and convenient in situ optical measurement of pressure, and with the appropriate biocompatible materials this device can be implanted for IOP measurements. Different testing media have been used to verify the efficacy of the device in different environments. In IPA and water, the device can realize continuous pressure measurement. By improving the channel structure and increasing the number of turns in the spiral or the moment arm of the sensor, the pressure response can be greatly enhanced.

Although specific embodiments and exemplary embodiments are disclosed herein, it is expected that persons skilled in the art can and will design alternative passive mechanical pressure sensors and methods to produce the passive mechanical pressure sensors that are within the scope of the following claims either literally or under the Doctrine of Equivalents.

What is claimed is:

1. An implantable mechanical passive pressure sensor comprising:

at least one micromachined flexible closed hollow body having first and second ends, said body being disposed on a substrate and describing at least one curve, wherein one of said ends is affixed to said substrate and the second of said ends and at least the portion of the body adjacent to said second end is allowed to move within a two-dimensional plane, wherein the pressure within said closed body is fixed, and wherein the arc of the at least one curve of the body is defined by the relative pressure between the internal pressure of the body and the surrounding environment, such that a change in the pressure surrounding the body causes a change in the arc of the at least one curve resulting in a measurable displacement of the second end of said body relative to the substrate, and wherein the displacement of the second end of said body provides a measurement of the environmental pressure surrounding the body, said displacement capable of being monitored visually.

2. The implantable mechanical passive pressure sensor defined in claim 1, wherein the extent of the curve defined by the body is described by the coiled angle of the body (θ) such that θ is at least 360°.

3. The implantable mechanical passive pressure sensor defined in claim 2, wherein the body is formed as a bourdon tube.

4. The implantable mechanical passive pressure sensor defined in claim 2, wherein the first end is disposed at the center of the spiral defined by the body.

5. The implantable mechanical passive pressure sensor defined in claim 2, wherein the first end is disposed at the exterior of the spiral defined by the body.

6. The implantable mechanical passive pressure sensor defined in claim 1, wherein the extent of the curve defined by the body is described by the coiled angle of the body (θ) such that θ is less than 360°.

7. The implantable mechanical passive pressure sensor defined in claim 6, wherein the body is formed as a hook.

8. The implantable mechanical passive pressure sensor defined in claim 1, wherein the first end is central to the spiral of the body and the second end further comprises a straight indicator arm distal to the curve defined by the body.

9. The implantable mechanical passive pressure sensor defined in claim 8, wherein the sensor comprises at least two flexible closed hollow bodies disposed on the substrate such that the second ends of each of the hollow bodies are in a diametric collinear arrangement such that when the pressure of the surrounding atmosphere changes the second ends of the at least two bodies are displaced in opposite directions.

10. The implantable mechanical passive pressure sensor defined in claim 1, wherein the body comprises a plurality of curved sections each of said curved sections being linked end to end with other curved sections in a zigzag arrangement, wherein the curved section at the first end of the body is fixedly attached to the substrate and the remaining curved sections are free to move, such that a change in the pressure surrounding the body produces a linear displacement of the body axially away from the first end.

11. The implantable mechanical passive pressure sensor defined in claim 1, wherein the sensor comprises a plurality of such bodies disposed on a single substrate.

12. The implantable mechanical passive pressure sensor defined in claim 11, wherein the bodies are arranged in a regular array.

13. The implantable mechanical passive pressure sensor defined in claim 1, wherein the aspect ratio between the height and width of the body is greater than 1.

14. The implantable mechanical passive pressure sensor defined in claim 1, wherein the displacement of the second end is both angular and radial.

15. The implantable mechanical passive pressure sensor defined in claim 1, wherein the displacement of the second end is optically measurable.

16. The implantable mechanical passive pressure sensor defined in claim 15, wherein the displacement may be measured with standard ophthalmologic equipment selected from the group consisting of stereoscopes and magnifiers.

17. The implantable mechanical passive pressure sensor defined in claim 1, wherein the fixed pressure within the body is about 1 atm.

18. The implantable mechanical passive pressure sensor defined in claim 1, wherein the sensor has a sensitivity of at least 0.22 degree/mmHg.

19. The implantable mechanical passive pressure sensor defined in claim 1, wherein the sensor has a sensitivity of at least 0.13 degree/mmHg.

20. The implantable mechanical passive pressure sensor defined in claim 1, wherein the sensor is made of a biocompatible material.

21. The implantable mechanical passive pressure sensor defined in claim 1, wherein the biocompatible material is parylene.

22. The implantable mechanical passive pressure sensor defined in claim 21, wherein the parylene is selected from the group consisting of parylene C, parylene N, parylene D, parylene F, parylene A, parylene AM, parylene HT.

23. The implantable mechanical passive pressure sensor defined in claim 1, wherein the pressure sensor is designed for implantation into the eye for measuring the IOP.

24. The implantable mechanical passive pressure sensor defined in claim 1, further comprising at least one measurement fiducials disposed on the substrate adjacent to the second end to provide a scale for determining the scope of the displacement.

25. The implantable mechanical passive pressure sensor defined in claim 1, wherein the body is disposed within a depression on the substrate.

26. An intraocular passive pressure sensor for measuring the intraocular pressure, comprising:

at least one micromachined flexible closed hollow body formed of a biocompatible material having first and second ends, said body being disposed on a substrate and describing at least one curve, wherein one of said ends is affixed to said substrate and the second of said ends and at least the portion of the body adjacent to said second end is allowed to move within a two-dimensional plane, wherein the pressure within said closed body is fixed, and wherein the arc of the at least one curve of the body is defined by the relative pressure between the internal pressure of the body and the surrounding environment, such that a change in the pressure surrounding the body causes a change in the arc of the at least one curve resulting in a measurable displacement of the second end of said body relative to the substrate, and wherein the displacement of the second end of said body provides a measurement of the environmental pressure surrounding the body, said displacement capable of being monitored visually.

* * * * *